(12) United States Patent
Biedermann et al.

(10) Patent No.: US 9,247,965 B2
(45) Date of Patent: Feb. 2, 2016

(54) POLYAXIAL BONE ANCHORING DEVICE WITH ENLARGED PIVOT ANGLE

(75) Inventors: Lutz Biedermann, VS-Villingen (DE); Martin Meer, Vöhringen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 311 days.

(21) Appl. No.: 13/586,454

(22) Filed: Aug. 15, 2012

(65) Prior Publication Data

US 2013/0096620 A1    Apr. 18, 2013

Related U.S. Application Data

(60) Provisional application No. 61/525,092, filed on Aug. 18, 2011.

(30) Foreign Application Priority Data

Aug. 18, 2011    (EP) .................................... 11178035

(51) Int. Cl.
  *A61B 17/04*    (2006.01)
  *A61B 17/70*    (2006.01)
  *A61B 17/86*    (2006.01)

(52) U.S. Cl.
  CPC .............. *A61B 17/70* (2013.01); *A61B 17/7037* (2013.01); *A61B 17/8605* (2013.01)

(58) Field of Classification Search
  CPC .................. A61B 17/7037; A61B 17/8605
  USPC .................................................. 606/308–305
  See application file for complete search history.

(56) References Cited

U.S. PATENT DOCUMENTS

| 6,736,820 B2 | 5/2004 | Biedermann et al. |
| 7,476,239 B2 | 1/2009 | Jackson |

(Continued)

FOREIGN PATENT DOCUMENTS

| CN | 101652106 A | 2/2010 |
| CN | 101754725 A | 6/2010 |

(Continued)

OTHER PUBLICATIONS

Extended European Search Report for European Application No. 11178035.9, extended European Search Report dated Dec. 7, 2011 and mailed Dec. 19, 2011 (7 pgs.).

*Primary Examiner* — Eduardo C Robert
*Assistant Examiner* — Stuart S Bray
(74) *Attorney, Agent, or Firm* — Christie, Parker & Hale, LLP (57) ABSTRACT

A polyaxial bone anchoring device includes an anchoring element having a shank and a head, a receiving part having a first end and a second end, a central axis, and an accommodation space for accommodating the head, the accommodation space having an opening at the second end, a sleeve-like insert piece configured to be arranged around a portion of the head and to be arranged in and to pivot in the accommodation space, and a pressure member including a portion configured to exert pressure onto the head, wherein the anchoring element and insert piece are pivotable with respect to the receiving part such that respective angles formed by a central axis of the insert piece with the central axis of the receiving part and a central axis of the anchoring element are adjustable, and can be locked by exerting pressure with the pressure member onto the head.

22 Claims, 8 Drawing Sheets

(56) References Cited

U.S. PATENT DOCUMENTS

| | | |
|---|---|---|
| 7,776,067 B2 * | 8/2010 | Jackson .................. 606/246 |
| 7,967,850 B2 * | 6/2011 | Jackson .................. 606/301 |
| 2004/0097933 A1 * | 5/2004 | Lourdel et al. ............ 606/61 |
| 2005/0049588 A1 * | 3/2005 | Jackson .................. 606/61 |
| 2005/0216003 A1 * | 9/2005 | Biedermann et al. ...... 606/61 |
| 2006/0173456 A1 * | 8/2006 | Hawkes et al. ........... 606/61 |
| 2006/0271047 A1 * | 11/2006 | Jackson .................. 606/61 |
| 2007/0118123 A1 * | 5/2007 | Strausbaugh et al. ..... 606/61 |
| 2007/0123862 A1 * | 5/2007 | Warnick .................. 606/61 |
| 2008/0004625 A1 * | 1/2008 | Runco et al. ............. 606/73 |
| 2008/0009862 A1 * | 1/2008 | Hoffman ................. 606/61 |
| 2008/0015579 A1 * | 1/2008 | Whipple ................. 606/61 |
| 2008/0154315 A1 * | 6/2008 | Jackson .................. 606/309 |
| 2008/0234761 A1 * | 9/2008 | Jackson .................. 606/309 |
| 2008/0269809 A1 * | 10/2008 | Garamszegi ............. 606/305 |
| 2009/0062866 A1 * | 3/2009 | Jackson .................. 606/301 |
| 2009/0093844 A1 * | 4/2009 | Jackson .................. 606/254 |
| 2009/0240290 A1 * | 9/2009 | Choi ..................... 606/308 |
| 2009/0299414 A1 | 12/2009 | Jackson |
| 2010/0030280 A1 * | 2/2010 | Jackson .................. 606/305 |
| 2010/0131018 A1 * | 5/2010 | Konieczynski et al. ..... 606/308 |
| 2010/0191293 A1 * | 7/2010 | Jackson .................. 606/302 |
| 2010/0198272 A1 * | 8/2010 | Keyer et al. .............. 606/302 |
| 2010/0211114 A1 * | 8/2010 | Jackson .................. 606/302 |
| 2010/0298891 A1 * | 11/2010 | Jackson .................. 606/308 |
| 2011/0009911 A1 * | 1/2011 | Hammill et al. .......... 606/308 |
| 2012/0136395 A1 * | 5/2012 | Biedermann et al. ...... 606/279 |
| 2012/0179212 A1 * | 7/2012 | Jackson et al. ........... 606/328 |
| 2013/0096620 A1 * | 4/2013 | Biedermann et al. ...... 606/279 |
| 2013/0138162 A1 * | 5/2013 | Kang et al. .............. 606/308 |
| 2013/0211465 A1 * | 8/2013 | Savage ................... 606/308 |
| 2013/0274817 A9 * | 10/2013 | Jackson .................. 606/309 |
| 2013/0296951 A1 * | 11/2013 | Jackson et al. ........... 606/308 |
| 2014/0058458 A1 * | 2/2014 | Barrus et al. ............. 606/308 |
| 2014/0058459 A1 * | 2/2014 | Courtney et al. .......... 606/308 |
| 2014/0128927 A1 * | 5/2014 | Jackson .................. 606/305 |

FOREIGN PATENT DOCUMENTS

| | | |
|---|---|---|
| JP | 2006-504505 A | 2/2006 |
| JP | 2010-520024 A | 6/2010 |
| WO | WO 2004/041100 A1 | 5/2004 |
| WO | WO 2007/075454 A1 | 7/2007 |
| WO | WO 2008/112114 A1 | 9/2008 |
| WO | WO 2008/124772 A1 | 10/2008 |
| WO | WO 2008/153723 A1 | 12/2008 |
| WO | WO 2009/015100 A2 | 1/2009 |

* cited by examiner

POLYAXIAL BONE ANCHORING DEVICE WITH ENLARGED PIVOT ANGLE

CROSS-REFERENCE TO RELATED APPLICATION(S)

The present application claims the benefit of U.S. Provisional Patent Application Ser. No. 61/525,092, filed Aug. 18, 2011, the contents of which are hereby incorporated by reference in their entirety, and claims priority to European Patent Application EP 11 178 035.9, filed Aug. 18, 2011 the contents of which are hereby incorporated by reference in their entirety.

BACKGROUND

1. Field of Invention

The invention relates to a polyaxial bone anchoring device with an enlarged pivot angle. The bone anchoring device includes a bone anchoring element for anchoring in a bone or a vertebra and a receiving part for coupling the bone anchoring element to a stabilization element such as a spinal rod, wherein the bone anchoring element is pivotable in the receiving part and can be pivoted with an enlarged pivot angle relative to a central axis of the receiving part. An orientation of the enlarged pivot angle can be selected for a range of 360° around the central axis and can be automatically achieved by pivoting the receiving part relative to the bone anchoring element. The polyaxial anchoring device is a modular device, wherein the receiving part and the bone anchoring element are connectable by introducing bone anchoring element, for example, from the bottom, into the receiving part.

2. Description of Related Art

A polyaxial bone anchoring device with an enlarged pivot angle is described in U.S. Pat. No. 6,736,820. This bone anchoring device includes a bone screw and a receiving part with a seat for the head of the bone screw. The screw member can be pivoted to at least one side by an enlarged angle, because the edge bounding the free end of the receiving part is of asymmetric construction. In a modified embodiment, an insert piece is provided, which has a spherical bottom as a seat for the head of the screw member.

US 2007/0118123 A1 describes a polyaxial bone anchor with increased angulation. The polyaxial bone anchor has a locking element shaped and configured to allow an anchoring member, e.g. a screw or a hook, to polyaxially rotate at large angles about a central axis of the bone anchor before compression locking the anchoring member within an anchor head.

SUMMARY

Although the polyaxial bone anchoring devices in the related art described above provide for enlarged angulation in a desired orientation, there is still a need for an improved polyaxial bone anchoring device in terms of simplicity of design and greater variety of applications.

It is an object of embodiments of the invention to provide a polyaxial bone anchoring device that allows adjustment of an orientation of an enlarged pivot angle, which has a simple design, and can be easily assembled, while also equally providing high efficiency or reliability of fixation.

The bone anchoring device according to some embodiments of the invention is a bottom loading polyaxial bone anchoring device, wherein an anchoring element can be inserted into a receiving part from a bottom of the receiving part. The bone anchoring device can be delivered by the manufacturer as a pre-assembled receiving part with a pressure member and, separate therefrom, one or more screw shanks or anchoring elements, some with pre-assembled or separate sleeve-like insert pieces. Such a polyaxial bone anchoring device can be assembled at any place and by anybody, in particular, by a surgeon or any personnel assisting him before or during surgery. Various shanks or anchoring elements with different diameter, thread form, length, or other features can be combined with a receiving part according to the actual clinical requirements in a particular clinical situation. This gives the surgeon a substantial choice of implants and reduces the number of parts that are including in an implant set or configuration.

By such modularity, costs of stock-holding can be lowered. The polyaxial bone anchoring device according to embodiments of the invention has few parts, each of which are of simple design. Therefore, the bone anchoring device is cost-effective to manufacture. It provides safe fixation, since a pressure for locking an angular position of the anchoring element with respect to the receiving part is applied effectively in an axial direction. This enables the design of the bone anchoring device to have smaller dimensions and a low profile structure. The bone anchoring device may be devoid of any flexible parts or portions. Therefore, it may be more reliable, even if during adjustment of the angular position, the orientation of the enlarged pivot angle is changed several times.

A maximum pivot angle of the bone anchoring element relative to the receiving part may be equal to or greater than 45° measured from a straight position. This renders the bone anchoring device particularly suitable for the application of lateral mass fixation, for example, in the cervical spine.

A locking mechanism for locking the anchoring element and the sleeve-like insert piece provides for a high clamping force on a small surface. Therefore, the locking mechanism may be more efficient.

Meanwhile, although in a lower portion of the receiving part, an insert member may be arranged that needs space for placement, an upper position of the receiving part can still have a small size.

BRIEF DESCRIPTION OF THE DRAWINGS

Further features and advantages of the invention will become apparent from the description of embodiments by means of the accompanying drawings. In the drawings.

DETAILED DESCRIPTION

As shown in FIGS. 1 to 4, a polyaxial bone anchoring device according to a first embodiment includes a bone anchoring element 1 in the form of, for example, a bone screw having a threaded shank 2 and a head 3. The head 3 typically has a spherically-shaped outer surface portion 3a and a recess 3b at its free end for engagement with a driver or tool. The head 3 is configured to be held in a receiving part 4 that couples the bone anchoring element 1 to a stabilization rod 100. In the receiving part 4, a sleeve-like insert piece 5 providing a seat for the head 3 of the bone anchoring element 1 and a pressure member 6 for exerting pressure onto the head 3 can be arranged. Furthermore, a fixation element in the form of, for example, a fixation screw 7 may be provided for securing and fixing the rod 100 in or relative to the receiving part 4.

The receiving part 4 has a top end 4a and a bottom end 4b, an axis C defining a central axis of the polyaxial bone anchoring device, and a coaxial bore 8 extending from the top end 4a in a direction of the bottom end 4b. Adjacent to the top end 4a, a substantially U-shaped recess 9 is provided that forms a channel for receiving the rod 100. By means of the recess 9, two free legs are formed which are each provided with an internal thread 10 that cooperates with the fixation screw 7.

The coaxial bore 8 opens into an accommodation space 11 provided in a tower part of the receiving part 4. The accommodation space 11 has a lower opening 12 at the bottom end 4b of the receiving part 4, and is shaped as a portion of a hollow sphere, including a largest inner diameter D. By the accommodation space 11, a seat for the sleeve-like insert piece 5 is provided, such that the seat and the sleeve-like insert piece 5 form a ball and socket joint. It should be noted that the seat can also be tapered, or can have any other shape that can be used to realize a ball and socket joint. An inner diameter of the lower opening 12 is slightly smaller than the largest inner diameter D of the accommodation space 11.

Adjacent the opening 12, the receiving part 4 includes a threaded portion 13 with an internal thread. A height of the threaded portion 13 is such that it includes only a few thread turns, i.e., at least one thread turn and at a maximum just so many thread turns that the sleeve-like insert piece 5 can freely pivot in the accommodation space 11 once having passed the threaded portion 13 during insertion. In any case, the threaded portion 13 extends from the lower opening 12 to a distance from the portion of the accommodation space 11 having the largest inner diameter D.

It shall be further noted that an inner diameter of the coaxial bore 8 does not need to be constant between the top end 4a and the accommodation space 11. The coaxial bore 8 may have different portions with different diameters.

The sleeve-like insert piece 5 will be explained with reference to FIGS. 3, 4, and 7 to 10. The sleeve-like insert piece 5 has an upper edge 5a and a lower edge 5b. Between the upper edge 5a and the lower edge 5b, a threaded outer surface portion 51 is provided. The thread corresponds to the thread of the threaded portion 13 of the receiving part 4. Furthermore, the threaded outer surface portion 51 is spherically-shaped. Dimensions of the threaded outer surface portion 51 are such that the sleeve-like insert piece 5 is insertable through the opening 12 by screwing, and once the insert piece 5 has passed the threaded portion 13, the insert piece 5 can pivot and rotate in the receiving part 4 when the insert piece 5 is in the seat provided by the accommodation space 11. The outer surface of the insert piece 5 can also be only partially threaded, with the threaded portion 51 including, for example, the portion of the insert piece 5 with the largest diameter.

The sleeve-like insert piece 5 is hollow and includes a central portion 52 that is spherically-shaped, with a radius corresponding to a radius of the spherically-shaped outer surface portion 3a of the head 3 of the anchoring element 1. A lower end of this central portion 52 forms a shoulder 53. An inner diameter of the shoulder 53 is smaller than a largest outer diameter of the spherical head 3, such that the head 3 can rotate and pivot in the central spherical portion 52 of the sleeve-like insert piece 5, similar to a ball and socket joint. Between the shoulder 53 and the lower edge 5b, a tapered portion 54 can be provided that tapers outward to allow angulation of an inserted bone anchoring element 1 until the shank 2 comes into contact with the lower edge 5b. Between the spherical central portion 52 and the upper edge 5a, a tapered portion 55 is provided that tapers outwards. An inner diameter of the tapered portion 55 and of the transition between the tapered portion 55 and the spherical central portion 52 may be greater than the largest outer diameter of the head 3, so that the head 3 can be inserted from the upper edge 5a.

Figure 1:
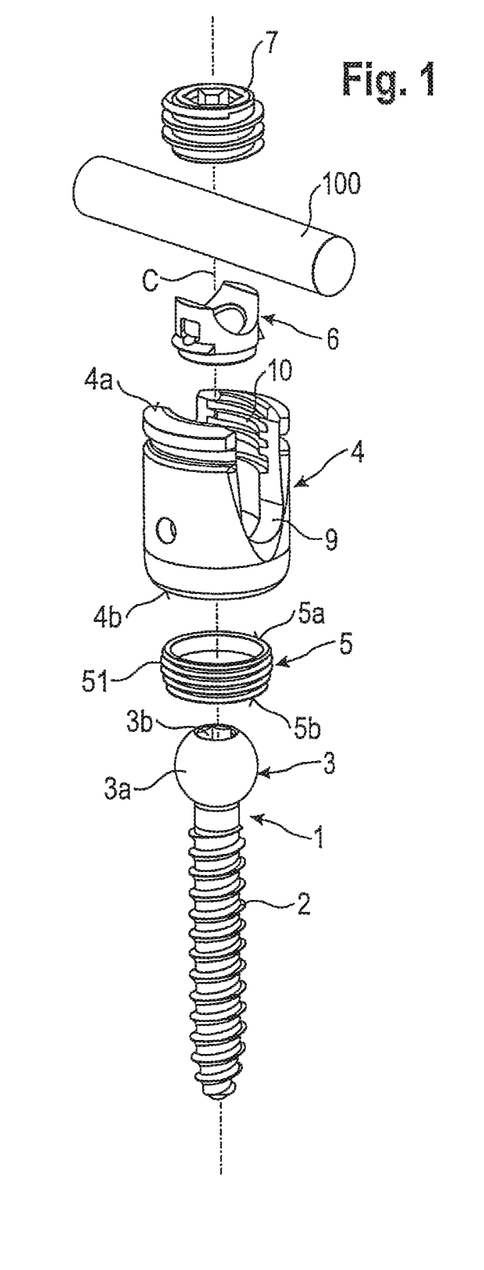
FIG. 1 shows a perspective exploded view of a polyaxial bone anchoring device with a spinal rod according to an embodiment of the invention.
Figure 2:
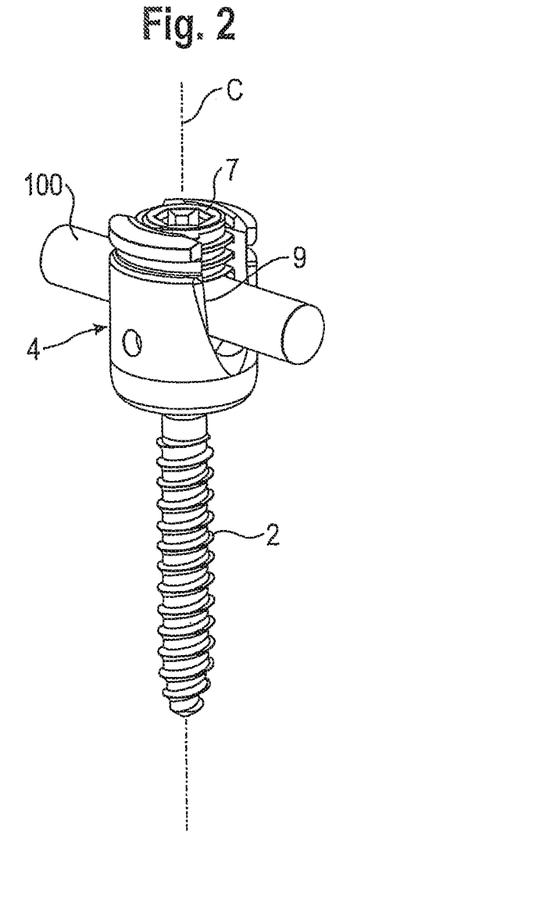
FIG. 2 shows a perspective view of the bone anchoring device of FIG. 1 in an assembled state.
Figure 3:
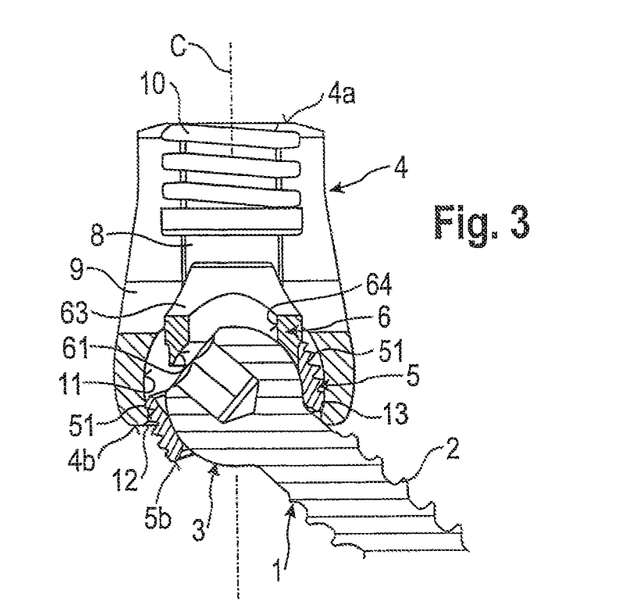
FIG. 3 shows a cross-sectional view of the bone anchoring device of FIGS. 1 and 2 in the assembled state, without a rod or a fixation screw, the section taken along an axis of an inserted rod.
Figure 4:
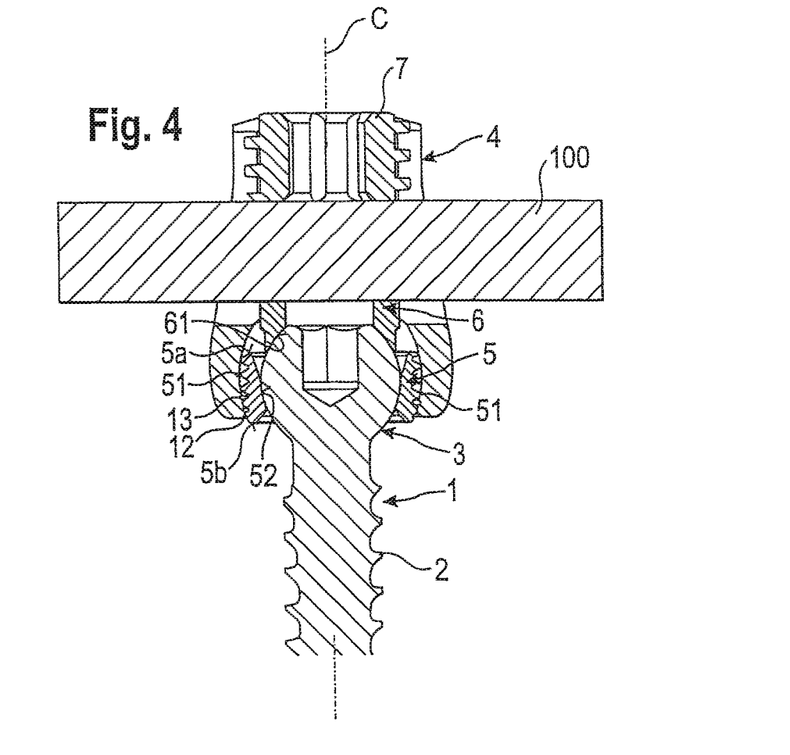
FIG. 4 shows a cross-sectional view of the bone anchoring device of FIGS. 1 and 2 in the assembled state, with inserted rod and fixation screw, the section taken along the rod axis.
Figures 5, 6:
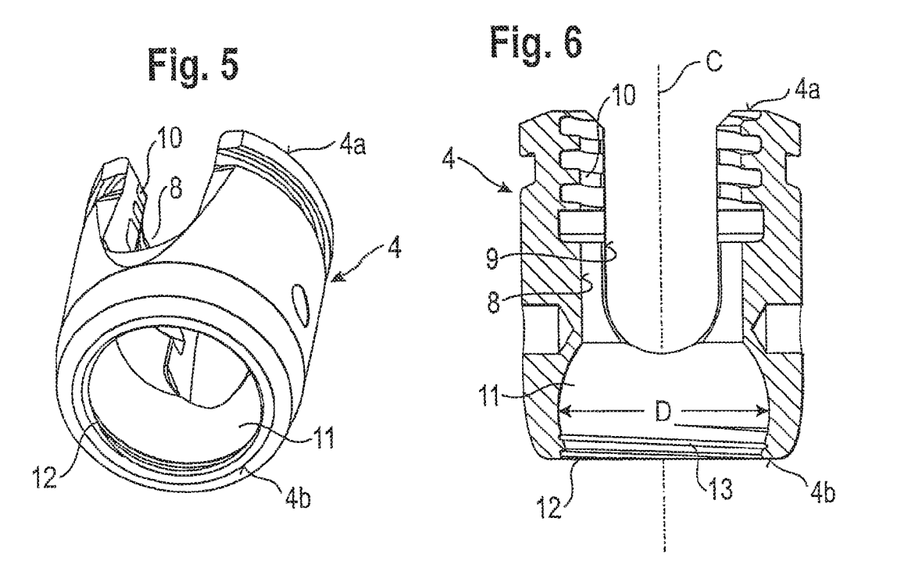
FIG. 5 shows a perspective view from a bottom of a receiving part of the bone anchoring device according to FIGS. 1 to 4.
FIG. 6 shows a cross-sectional view of the receiving part of FIG. 5, the section taken perpendicular to the rod axis.
Figure 7:
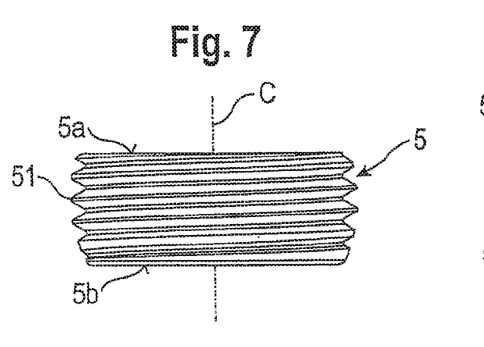
FIG. 7 shows a side view of a sleeve-like insert piece according to a first embodiment.
Figure 8:
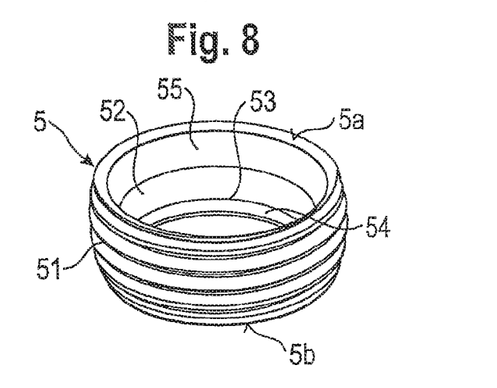
FIG. 8 shows a perspective view from above of the sleeve-like insert piece of FIG. 7.
Figure 9:
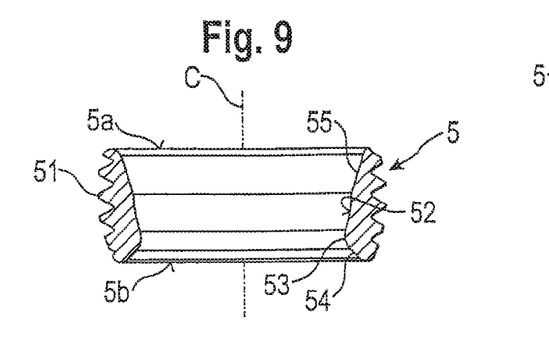
FIG. 9 shows a cross-sectional view of the sleeve-like insert piece of FIGS. 7 and 8, the section taken in a plane containing a central axis of the insert piece.
Figure 10:
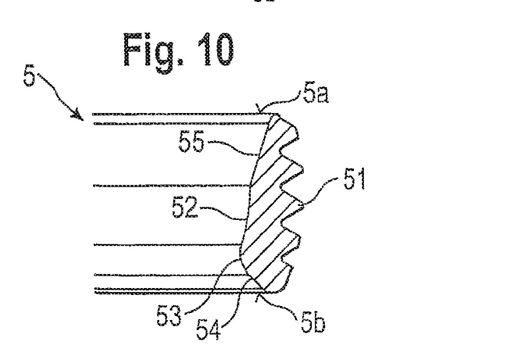
FIG. 10 shows an enlarged portion of the sleeve-like insert piece of FIG. 9.
Figure 11:
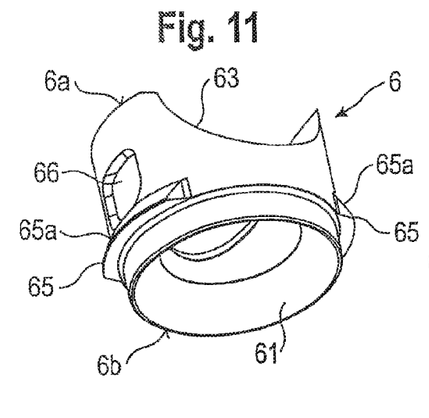
FIG. 11 shows a perspective view of a pressure member of the polyaxial bone anchoring device according to an embodiment of the invention.
Figure 12:
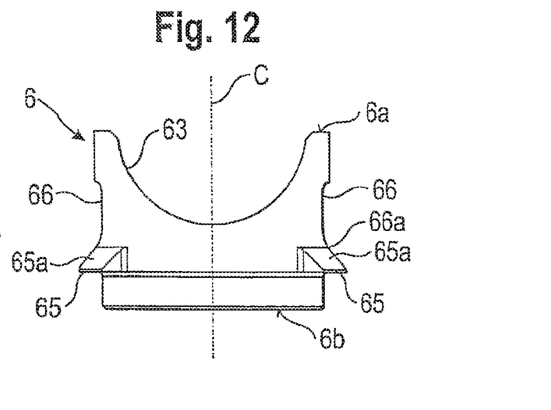
FIG. 12 shows a side view of the pressure member of FIG. 11 perpendicular to the rod axis.
Figure 13:
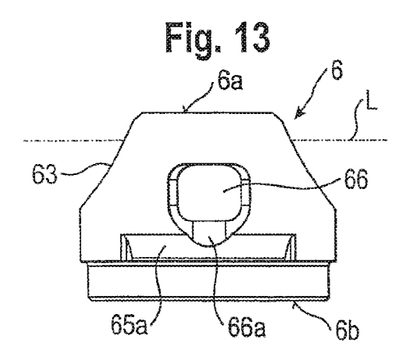
FIG. 13 shows a side view of the pressure member of FIG. 11 along the rod axis.
Figure 14:
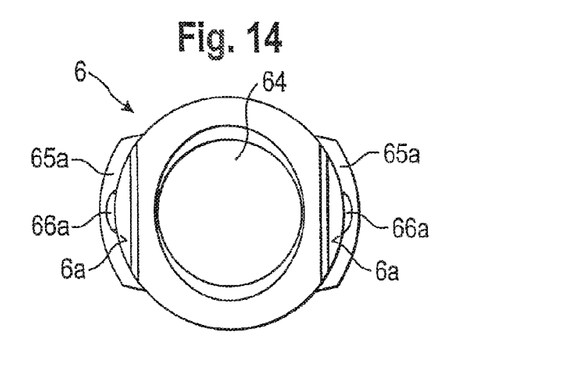
FIG. 14 shows a top view of the pressure element of FIG. 11.

Spherical center points of the spherical central portion 52 and of the outer spherical portion 51 may be offset from each other in such a way that the center point of the central spherical portion 52 is shifted towards the lower edge 5b relative to the center point of the outer spherical portion 51. By means of this, a range of angulation of the bone anchoring element 1 can be further increased. A height of the sleeve-like insert piece 5 in an axial direction along the central axis C is less than a height of the head 3 in an axial direction, such that when the head 3 is inserted into the sleeve-like insert piece 5, a portion of the spherical outer surface 3a of the head 3 projects from the upper edge 5a of the sleeve-like insert piece 5, as shown in FIGS. 3 and 4. An inner diameter of the central spherical portion 52 is dimensioned such that the head 3 can hold the sleeve-like insert piece 5 by a slight tension caused by a friction fit. By means of this, a torque necessary for screwing in of the anchoring element 1 with the sleeve-like insert piece 5 can be transferred from the anchoring element 1 to the sleeve-like insert piece 5.

The sleeve-like insert piece 5 is rigid, i.e., does not have any flexible portions such as, for example, slits that would render the insert piece 5 more flexible.

The pressure member 6 is shown in particular in FIGS. 3, 4, and 11 to 14. The pressure member 6 is substantially cylindrical with an outer diameter that allows it to move within the coaxial bore 8 and the accommodation space 11 of the receiving part 4. The pressure member 6 it has an upper end 6a and a lower edge 6b. Adjacent its lower edge 6b, a spherical recess 61 with a spherical shape that matches the spherical shape of the outer spherical surface portion 3a of the head 3 is provided.

At the upper end 6a, the pressure member 6 has a cylindrical recess 63 for receiving the rod 100 therein. Furthermore, the pressure member 6 has a coaxial bore 64 for allowing access to the head 3 with a tool. The coaxial bore 64 is also configured to allow a portion of the head 3 to extend therethrough when the bone anchoring element is in a pivoted condition, as shown, for example, in FIG. 3. A height of the pressure member 6 in an axial direction along the central axis C is such that when the fixation screw 7 is tightened, the fixation screw 7 presses onto the rod 100, which then presses onto the pressure member 6, which in turn acts onto the head 3 of the bone anchoring element 1.

At an outer surface of the pressure member 6, two outwardly extending projections 65 that each extends over a length of the pressure member 6 in a circumferential direction, are provided. Each projection 65 has an upper surface 65a facing the upper end 6a having a spherical shape matching the hollow spherical shape of the accommodation space 11. The projections 65 may be offset by 180° and may be located or oriented at a position perpendicular to the rod axis L as shown, for example, in FIGS. 12 and 13. The projections 65a may be located at a distance from the lower edge 6b and at a distance from a bottom of the cylindrical recess 63 along central axis C. Above the projections 65, two recesses 66 are provided offset from each other by 180°. The recesses each have a portion 66a extending into the spherical upper surface 65a of the projections 65. The recesses 66 provide a space for material of the inner wall of the receiving part 4 generated by crimping, as explained below.

Figure 15:
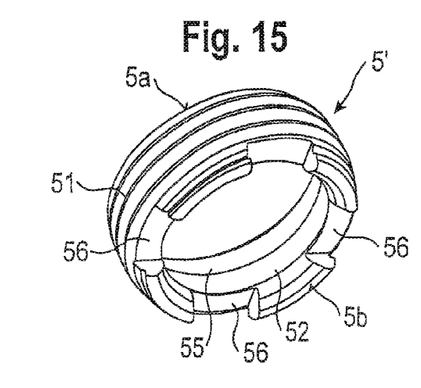
FIG. 15 shows a perspective view from a bottom of another embodiment of a sleeve-like insert piece.
Figure 16:
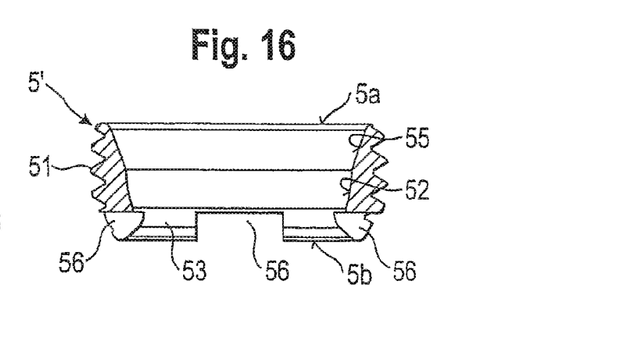
FIG. 16 shows a cross-sectional view of the sleeve-like insert piece of FIG. 15, the section taken in a plane containing a central axis of the insert piece.

A further embodiment of the sleeve-like insert piece 5' is shown in FIGS. 15 and 16. The sleeve-like insert piece according to FIGS. 15 and 16 differs from the sleeve-like insert piece 5 described before by the additional provision of a drive feature for engagement with a tool to screw in the sleeve-like insert piece 5' into the receiving part 4. All other portions of the insert piece 5' are the same as those in the first embodiment and are indicated by the same reference numerals. The descriptions thereof will therefore not be repeated. The sleeve-like insert piece 5' has at its lower edge 5b slits 56 that serve as an engagement portion for a tool. The slits 56 can have any shape that allows for engagement with a tool. A plurality of slits 56 may be provided in a circumferential direction. In embodiments where the sleeve-like insert piece 5' is used, the head 3 may not need to be clamped in the sleeve-like insert piece 5'.

The bone anchoring device as a whole or in part may be made of a bio-compatible material, such as a bio-compatible metal, for example titanium or stainless steel, a bio-compatible alloy, such as nickel-titanium alloys, for example, Nitinol, or of bio-compatible plastic materials, such as, for example, polyetheretherketone (PEEK).

Figures 17, 18, 19, 20, 21, 22:
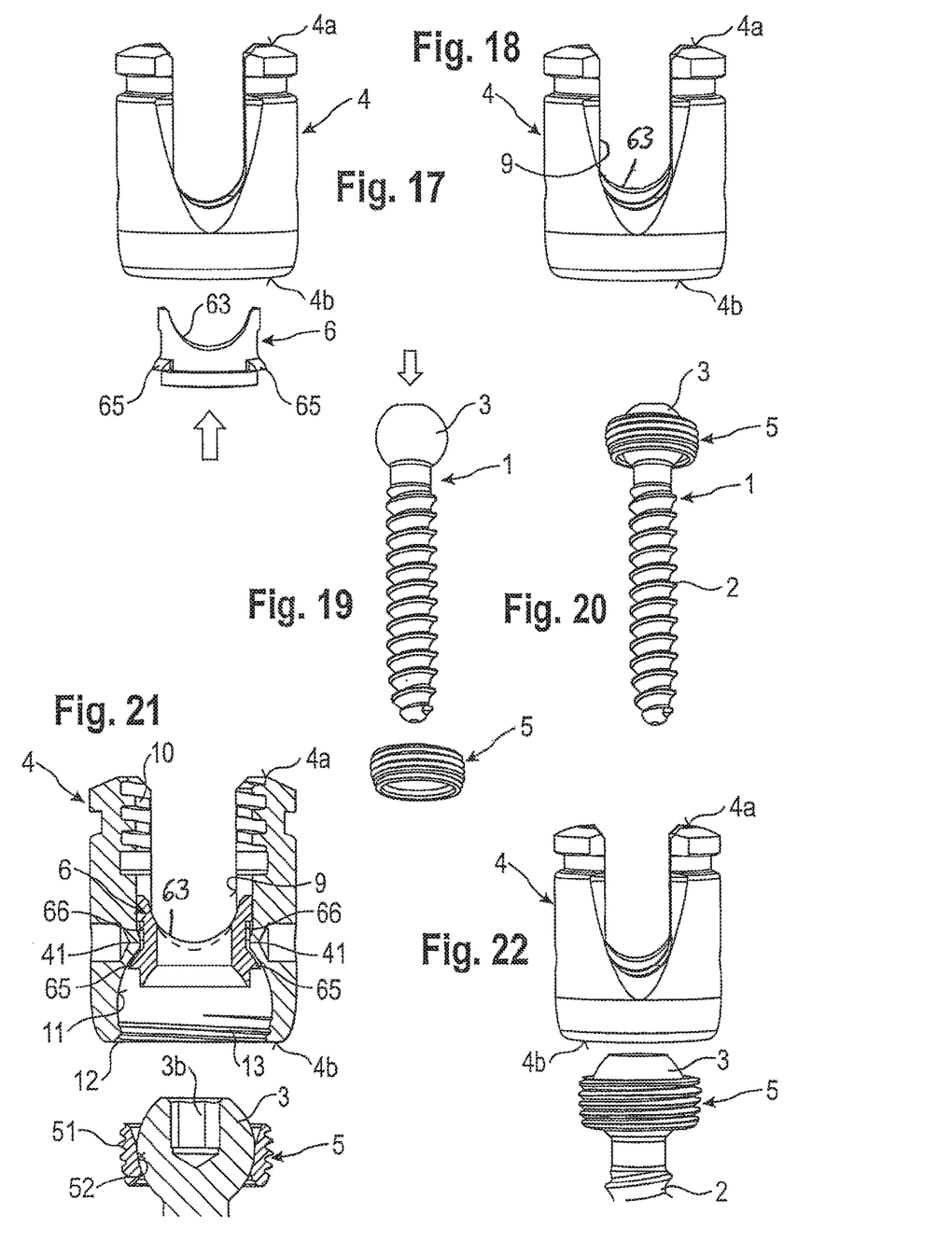
FIGS. 17 to 28 show steps of assembling the polyaxial bone anchoring device according to an embodiment of the invention.

Steps of assembling the bone anchoring device according to embodiments of the invention will be explained with reference to FIGS. 17 to 28. FIG. 17 shows a side view of a first step of assembling the bone anchoring device. The pressure member 6 is introduced into the receiving part 4 through the lower opening 12 until its cylindrical recess 63, as shown in FIG. 18, projects slightly above the U-shaped recess 9 of the receiving part 4, and is aligned therewith. As shown in the sectional view according to FIG. 21, the pressure member 6 may be mounted to or held in the receiving part 4 by crimping, wherein with a crimping tool the inner wall of the receiving part 4 is slightly deformed to form deformed portions 41 protruding into the recesses 66. As the recesses 66 are larger in an axial direction than the deformed portions 41 the pressure member 6 can move slightly within the receiving part 4 in an axial direction. The receiving part 4 and the pressure member 6 may be pre-assembled and delivered in such a pre-assembled state.

The sleeve-like insert piece 5 is mounted to the bone anchoring element 1, as shown in a side view in FIGS. 19 and 20. The bone anchoring element 1 is introduced from the upper edge 5a into the sleeve-like insert piece 5 until the spherical head 3 rests in the spherically-shaped central portion 52 and is slightly clamped therein in some embodiments. A large variety of bone anchoring elements, each with or without a mounted sleeve-like insert piece, may be provided.

Figures 23, 24:
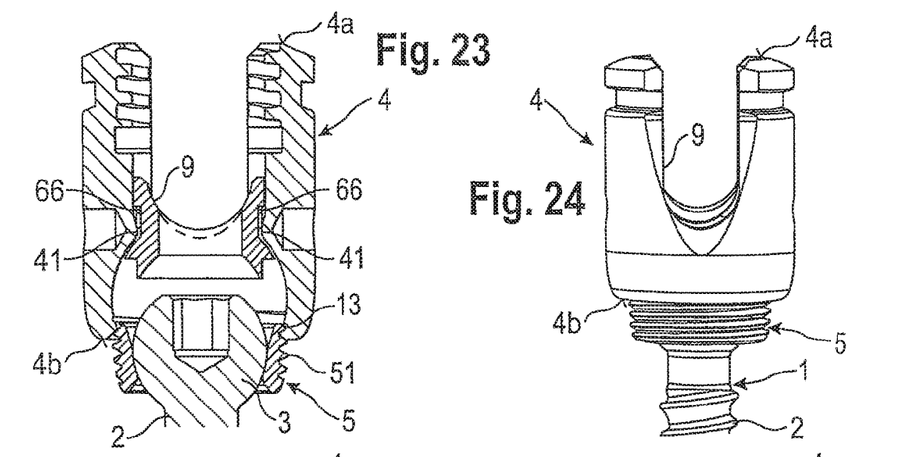

As can be seen in FIGS. 21 to 24, the bone anchoring element 1 with mounted sleeve-like insert piece 5 is introduced from the bottom end 4b into the receiving part 4. FIG. 21 shows a cross-sectional view of the polyaxial bone anchoring device with the section taken perpendicular to the rod axis. FIG. 22 shows a side view of the polyaxial bone anchoring device before assembling the bone anchoring element 1 with the receiving part 4. FIG. 23 shows a cross-sectional view of the bone anchoring device and FIG. 24 a side view thereof, wherein the bone anchoring element 1 is introduced into the receiving part 4 through the lower opening 12. The thread of the outer surface portion 51 of the sleeve-like insert piece 5 engages the threaded portion 13 of the receiving part 4. Because the sleeve-like insert piece 5 is slightly clamped onto the head 3 of the bone anchoring element 1, a torque applied to the shank 2 is transferred to the insert piece 5 to engage the threaded portion 13. When the sleeve-like insert piece 5 is used, a tool may be used to screw in the anchoring element 1 with the sleeve-like insert piece 5.

Figure 25:
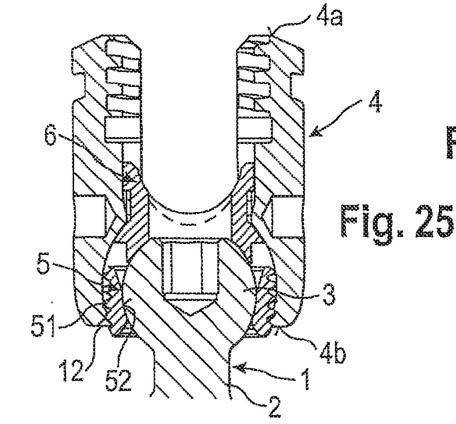
Figure 26:
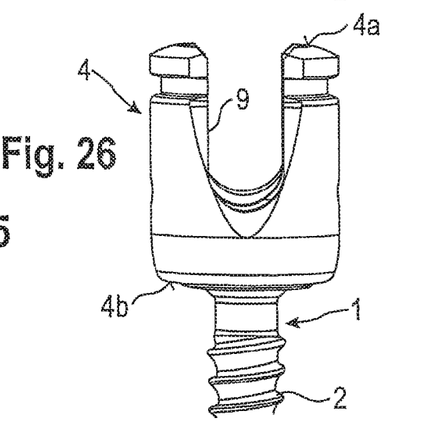

FIGS. 25 and 26 show a cross-sectional view and a corresponding side view of the polyaxial bone anchoring device, wherein the bone anchoring element 1 and the sleeve-like insert piece 5 have been completely inserted. In this position, the pressure member 6 is at its uppermost position, in which the upper spherical portions 65a of the projections 65 abut against the inner wall of the accommodation space 11. The head of the anchoring element 1 and the sleeve-like insert piece 5 are pivotable in the receiving part 4.

The assembly steps shown in FIGS. 19 to 26 can be performed by any person at any place. Therefore, a suitable polyaxial bone anchoring device can be selected from a great variety of bone anchoring elements that can each be assembled with receiving parts on demand.

Figure 27:
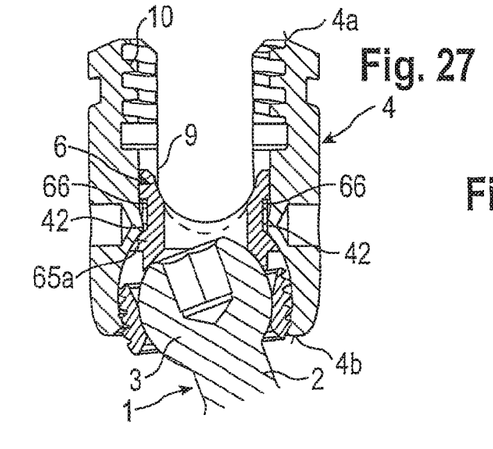
Figure 28:
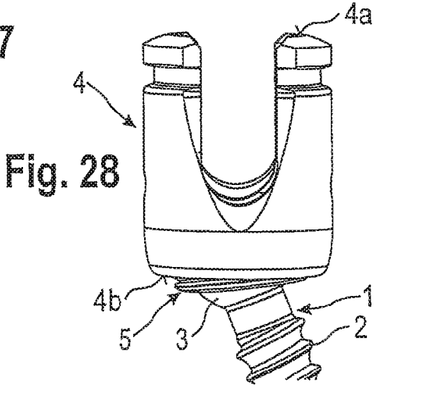
Figure 29:
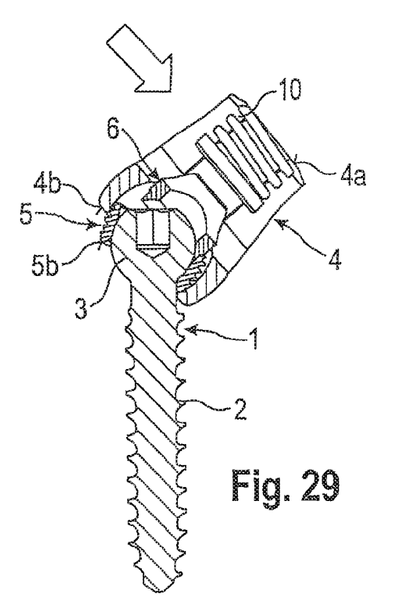
FIGS. 29 to 32 show steps of adjusting an angle of the bone anchoring element with respect to the receiving part of the polyaxial bone anchoring device according to an embodiment of the invention.

In a final step shown in FIGS. 27 and 28, wherein FIG. 27 shows a cross-sectional view and FIG. 28 a corresponding side view of the polyaxial bone anchoring device, the pressure member 6 may be further fixed by crimping. Through further crimping, the pressure member 6 is moved downward relative to receiving part 4 until pressure member 6 slightly presses onto the head 3 with the spherical recess 61 to exert a preload or friction force onto the head 3. By this additional crimping step, deformed portions 42 are generated that hold the pressure member 6 in a predetermined preliminary position. By adjusting the force of the crimping operation, a defined friction fit is achieved between the head 3 and the pressure member 6. The bone anchoring element 1 can then be pivoted only by overcoming the frictional force between the pressure member 6 and the head 3.

The assembly of the bone anchoring element 1 and the receiving part 4 with the second embodiment of the sleeve-like insert piece 5 is carried out in the same manner as the first embodiment, except that a tool can be used for engaging the slits 56 and rotating the sleeve-like insert piece 5'.

Figure 30:
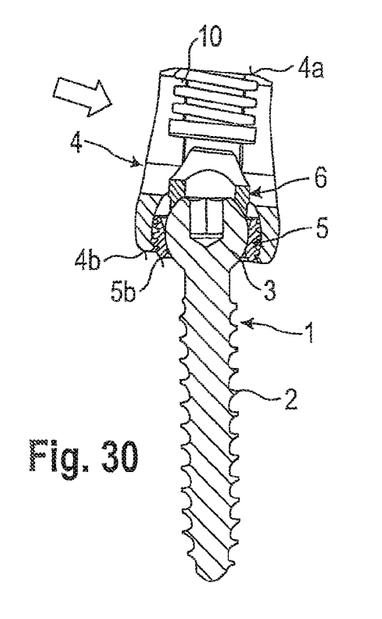

The steps of use of the bone anchoring device are shown by the cross-sectional views of FIGS. 29 to 32. The fixation screw and the rod are omitted in these exemplary figures. First, the anchoring element 1 is inserted in a bone part or in a vertebra. Usually, several bone anchoring devices are needed to fix a stabilization rod 100 to the bone parts or the vertebrae to be stabilized. After the bone anchoring elements 1 are inserted, one example of which is shown in FIGS. 29 to 32, the receiving part 4 can be adjusted by pivoting and/or rotating, in order to be able to insert the stabilization rod 100 into the U-shaped recess 9. In the condition shown in FIGS. 29 to 32, both the sleeve-like insert piece 5 and the head 3 of the bone anchoring element 1 are independently and freely pivotable. The sleeve-like insert piece 5 is rotatable and pivotable in the receiving part 4, and both are rotatable and pivotable with respect to the head 3 of the bone anchoring element 1. The sleeve-like insert piece 5 provides for an enlarged range of angulation compared to devices where the head 3 is directly received in the receiving part 5, because a distance between the shank 2 and the lower end 4b of the receiving part 4 is greater. Because the sleeve-like insert piece 5 is rotatable and pivotable within the receiving part 4, an enlarged range of angulation can be achieved at any position of the receiving part 4 with respect to the bone anchoring element 1 for 360° around the central axis C of the receiving part 4. As shown in FIG. 30, pivoting the receiving part 4 towards an opposite direction may also pivot the sleeve-like insert piece 5.

Figures 31A, 31B:
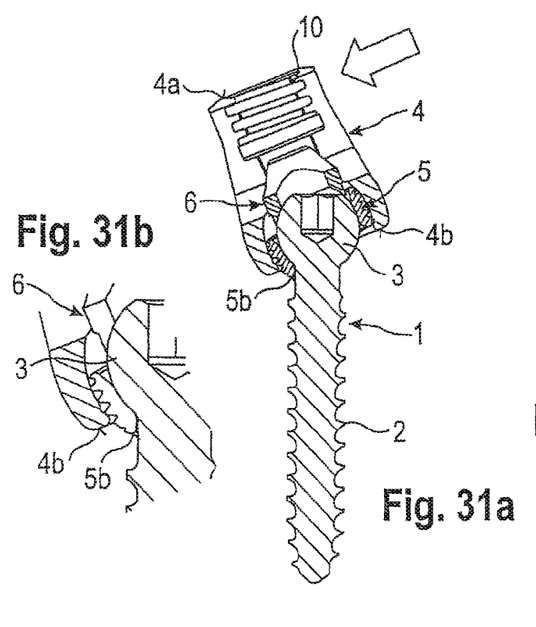
Figure 32:
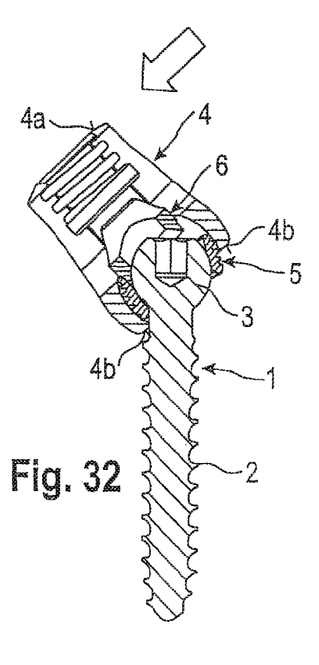

As shown in FIG. 31a and in the enlarged representation of FIG. 31b, further pivoting the receiving part 4 may in some cases essentially maintain a position of the sleeve-like insert piece 5. As soon as the shank 2 of the bone anchoring element 1 comes into contact with the lower edge 5b of the sleeve-like insert piece 5 as shown in FIGS. 31a and 31b, the sleeve-like insert piece 5 will also be pivoted. The shank 2 pushes the insert piece 5 until the shank 2 abuts against an edge of the lower opening 12 of the receiving part 4, as shown in FIG. 32. Hence, in FIG. 32, the receiving part 4 is pivoted at a maximum pivot angle with respect to the bone anchoring element 1. The maximum pivot angle to be achieved depends on the dimensions of the sleeve-like insert piece 5, the receiving part 4, and the bone anchoring element 1, but is typically equal to or greater than 45° measured from a straight or zero angle position.

While in FIGS. 29 to 32, an example is shown in which pivoting is carried out in a plane that contains the rod axis, it should be noted that the same steps can be carried out at any other direction for 360° around the central axis C of the receiving part 4.

The sleeve-like insert piece 5 together with the bone anchoring element 1 cannot escape from the lower opening 12 because of the obstacle provided by the threaded portion 13. The friction fit between the pressure member 6 and the head 3 of the anchoring element 1 has an effect where the receiving part 4 can be maintained provisionally at any position with respect to the bone anchoring element 1.

Finally, the rod 100 may be inserted and the inner screw 7 may be tightened to press the pressure element 6 onto the head 3, to lock the head 3 and the sleeve-like insert piece 5 simultaneously.

Further modifications of the embodiments described may also be conceivable. For example, for the bone anchoring element, all kinds of anchoring elements can be used and combined with the receiving part. Such anchoring elements may be, for example, screws of different length, with different diameters, canulated screws, screws with different thread forms, nails, hooks, etc. The head and the shank may also be separate parts that are connectable to each other.

Modifications of the receiving part may include, instead of the U-shaped recess which is perpendicular to the central axis, having a recess for the rod which is inclined or open to the side or which is in the form of a closed channel.

Figures 33, 34:
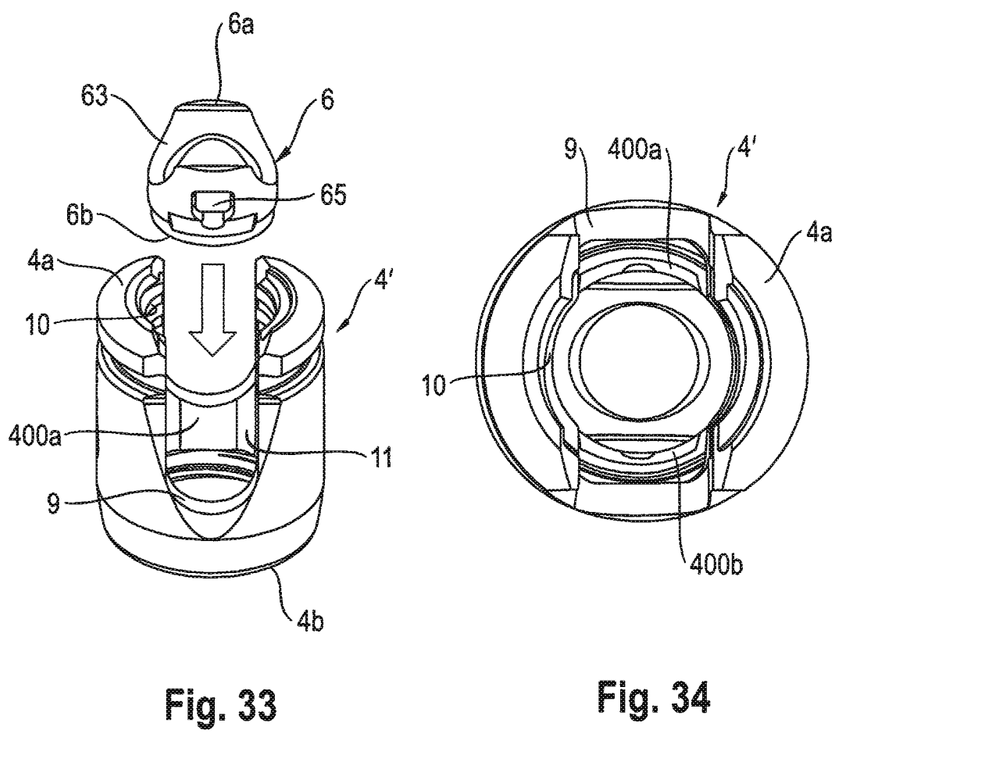
FIG. 33 shows a perspective view of a modified receiving part with pressure member.
FIG. 34 shows a top view of the modified receiving part of FIG. 33.

In another modified embodiment shown in FIGS. 33 and 34, in order to allow a pressure member 6 to be inserted from a top end 4a of a receiving part 4', the receiving part 4' has two opposed recesses 400a, 400b, along inner walls of coaxial bore 8 and accommodation space 11. The recesses 400a, 400b are aligned with U-shaped recess 9, and extend from a bottom of the U-shaped recess 9 into the accommodation space 11. A size of the recesses 400a, 400b is such that the pressure member 6 can be introduced from the top end 4a of the receiving part 4' when projections 65 are positioned in or aligned with the U-shaped recess 9. When the projections 65 enter the accommodation space 11, the pressure member 6 can be rotated, and a recess 63 of the pressure member 6 can be aligned with the U-shaped recess 9 of the receiving part 4'.

Other kinds of locking devices including outer nuts, outer caps, bayonet locking devices, or others are also possible. The locking device can also be a two part locking device having one locking element that locks the head of the anchoring element and another locking element that locks the rod. In some embodiments, the inner surface portion of the pressure member that contacts the head is not necessarily spherically-shaped. The inner surface portion can have any other shape that is suitable to exert pressure onto the head.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
    an anchoring element having a shank for anchoring to a bone and a head having a spherically-shaped outer surface portion;
    a receiving part having a first end and a second end, a central axis extending through the first end and the second end, a transverse channel at the first end for receiving a rod, and an accommodation space for accommodating the head, the accommodation space having an opening at the second end;
    a sleeve-like insert piece having a central axis and a seat for holding at least a portion of the head, wherein the insert piece is configured to be arranged in and to pivot in the accommodation space of the receiving part; and
    a pressure member configured to be arranged at least partially in the accommodation space, the pressure member comprising a portion configured to contact the head to exert pressure onto the head;

wherein when the head is in the seat of the insert piece and when the central axis of the receiving part and the central axis of the insert piece are coaxial, the insert piece is insertable into the accommodation space through the opening of the receiving part; and wherein when the head, the insert piece, and the pressure member are arranged in the receiving part, the anchoring element and insert piece are pivotable with respect to the receiving part, such that respective angles formed by the central axis of the insert piece with the central axis of the receiving part and by the central axis of the insert piece with a central axis of the anchoring element are both adjustable, and the insert piece can be locked relative to the receiving part and the anchoring element at the respective angles by exerting pressure with the pressure member onto the head.

2. The polyaxial bone anchoring device of claim 1, wherein the receiving part comprises a first engagement portion near the second end, and the insert piece comprises a second engagement portion for engaging the first engagement portion.

3. The polyaxial bone anchoring device of claim 2, wherein the first engagement portion and the second engagement portion comprise threaded portions.

4. The polyaxial bone anchoring device of claim 2, wherein the accommodation space has a portion with a largest diameter, and wherein the first engagement portion extends from the opening towards the portion of the accommodation space with the largest diameter.

5. The polyaxial bone anchoring device of claim 2, wherein the second engagement portion extends over a full outer surface of the insert piece.

6. The polyaxial bone anchoring device of claim 2, wherein the insert piece is insertable into the accommodation space by engaging the first engagement portion and the second engagement portion, and wherein when the insert piece is inserted in the accommodation space and the first engagement portion and the second engagement portion are disengaged, the insert piece is freely pivotable in the accommodation space.

7. The polyaxial bone anchoring device of claim 2, wherein when the insert piece is in the receiving part, the first engagement portion and the second engagement portion form a stop to prevent the insert piece from being removed from the receiving part.

8. The polyaxial bone anchoring device of claim 1, wherein the insert piece is configured to be held on the head by friction.

9. The polyaxial bone anchoring device of claim 1, wherein the insert piece has a first edge and a second edge, and wherein an engagement portion is provided at the second edge for engaging a tool.

10. The polyaxial bone anchoring device of claim 1, wherein the accommodation space defines a hollow spherically-shaped portion, and the insert piece has an outer spherically-shaped surface portion.

11. The polyaxial bone anchoring device of claim 1, wherein when the insert piece is arranged around the head and inserted in the receiving part, the insert piece and the anchoring element are independently pivotable relative to the receiving part when the shank of the anchoring element and an edge of the insert piece are out of contact.

12. The polyaxial bone anchoring device of claim 11, wherein when the shank of the anchoring element engages the edge of the insert piece, the anchoring element and the insert piece are pivotable together.

13. The polyaxial bone anchoring device of claim 1, wherein the insert piece has an inner spherical surface portion that forms the seat for the head.

14. The polyaxial bone anchoring device of claim 1, wherein the insert piece is rigid.

15. The polyaxial bone anchoring device of claim 1, wherein when the head, the insert piece, and the pressure member are in the receiving part, the pressure member is configured to be held in the receiving part at a position where the pressure member exerts a preload onto the head to clamp the head by friction at a first adjustable position before final locking of an angular position of the anchoring element relative to the receiving part.

16. The polyaxial bone anchoring device of claim 1, wherein the insert piece is rotationally symmetrical.

17. A method of coupling a rod to a bone or vertebra via a polyaxial bone anchoring device, the bone anchoring device comprising an anchoring element having a shank for anchoring to a bone and a head having a spherically-shaped outer surface portion, a receiving part having a first end and a second end, a central axis extending through the first end and the second end, a transverse channel at the first end for receiving a rod, and an accommodation space for accommodating the head, the accommodation space having an opening at the second end, a sleeve-like insert piece having a central axis and a seat for holding at least a portion of the head, wherein the insert piece is configured to be arranged in and to pivot in the accommodation space of the receiving part, and a pressure member configured to be arranged at least partially in the accommodation space, the pressure member comprising a portion configured to contact the head to exert pressure onto the head, and a fixation element, the method comprising:

connecting the anchoring element to the receiving part by introducing the insert piece and the head through the opening and into the accommodation space of the receiving part, wherein the insert piece and the head are insertable into the accommodation space when the head is in the seat of the insert piece and when the central axis of the receiving part and the central axis of the insert piece are coaxial, and wherein when the head, the insert piece, and the pressure member are arranged in the receiving part, the anchoring element and the insert piece are pivotable with respect to the receiving parts such that respective angles formed by the central axis of the insert piece with the central axis of the receiving part and by the central axis of the insert piece with a central axis of the anchoring element are both adjustable;

inserting the anchoring element into a bone or vertebra;

pivoting the receiving part relative to the anchoring element to adjust the respective angles of the insert piece relative to the receiving part and the anchoring element;

inserting a rod into the channel of the receiving part, wherein the pressure member is arranged between the rod and the anchoring element; and advancing the fixation element in the channel, such that the fixation element exerts pressure on the rod, the rod exerts pressure on the pressure member, and the pressure member exerts pressure onto the head of the anchoring element, to lock the insert piece relative to the receiving part and the anchoring element at the respective angles.

18. The method of claim 17, further comprising attaching the insert piece to the head of the anchoring element prior to connecting the anchoring element to the receiving part.

19. The method of claim 17, further comprising inserting the pressure member into the receiving part.

20. The method of claim 17, further comprising holding the pressure member at a first position when the anchoring element is connected to the receiving part and the rod is not inserted into the channel, such that the pressure member exerts a frictional force on the head of the anchoring element to hold the angular position of the receiving part relative to the anchoring element, wherein said position is adjustable by applying a force greater than the frictional force on the receiving part or the anchoring element.

21. A polyaxial bone anchoring device comprising:
an anchoring element having a shank for anchoring to a bone and a head having a spherically-shaped outer surface portion;
a receiving part having a first end and a second end, a central axis extending through the first end and the second end, a transverse channel at the first end for receiving a rod, and an accommodation space for accommodating the head, wherein the accommodation space has an opening at the second end and the receiving part has a first engagement portion near the opening;
a sleeve-like insert piece having an outer surface and a second engagement portion comprising a groove at the outer surface, wherein the insert piece is configured to be arranged around a portion of the head and to be arranged in and to pivot in the accommodation space of the receiving part; and
a pressure member configured to be arranged at least partially in the accommodation space, the pressure member comprising a portion configured to contact the head to exert pressure onto the head;
wherein when the insert piece is arranged around the head, the first engagement portion of the receiving part and the second engagement portion of the insert piece are configured to engage to facilitate insertion of the insert piece into the accommodation space through the opening of the receiving part; and
wherein when the head, the insert piece, and the pressure member are arranged in the receiving part, the anchoring element and insert piece are pivotable with respect to the receiving part, such that respective angles formed by a central axis of the insert piece with the central axis of the receiving part and by the central axis of the insert piece with a central axis of the anchoring element are both adjustable, and the insert piece can be locked relative to the receiving part and the anchoring element at the respective angles by exerting pressure with the pressure member onto the head.

22. A polyaxial bone anchoring device comprising:
an anchoring element having a shank for anchoring to a bone and a head having a spherically-shaped outer surface portion;
a receiving part having a first end and a second end, a central axis extending through the first end and the second end, a transverse channel at the first end for receiving a rod, and an accommodation space for accommodating the head, the accommodation space having an opening at the second end;
a sleeve-like insert piece having a threaded outer surface, wherein the insert piece is configured to be arranged around a portion of the head and to be arranged in and to pivot in the accommodation space of the receiving part; and
a pressure member configured to be arranged at least partially in the accommodation space, the pressure member comprising a portion configured to contact the head to exert pressure onto the head;
wherein when the insert piece is arranged around the head, the insert piece is insertable into the accommodation space through the opening of the receiving part; and
wherein when the head, the insert piece, and the pressure member are arranged in the receiving part, the anchoring element and insert piece are pivotable with respect to the receiving part, such that respective angles formed by a central axis of the insert piece with the central axis of the receiving part and by the central axis of the insert piece with a central axis of the anchoring element are both adjustable, and the insert piece can be locked relative to the receiving part and the anchoring element at the respective angles by exerting pressure with the pressure member onto the head.

* * * * *